(12) United States Patent
Miekka et al.

(10) Patent No.: US 6,378,518 B1
(45) Date of Patent: Apr. 30, 2002

(54) METHOD FOR PRODUCING UNIFORM SMALL DOSES OF FINELY DIVIDED SUBSTANCES

(76) Inventors: Richard George Miekka, 6735 14th St. South, St. Petersburg, FL (US) 33705; Richard Allan Fotland, One Crab Apple La., Franklin, MA (US) 02038

( * ) Notice: Subject to any disclaimer, the term of this patent is extended or adjusted under 35 U.S.C. 154(b) by 0 days.

(21) Appl. No.: 09/427,996

(22) Filed: Oct. 27, 1999

Related U.S. Application Data
(60) Provisional application No. 60/106,338, filed on Oct. 30, 1998.

(51) Int. Cl.7 .................. A61M 15/00; A61M 16/00; B05D 7/14; B65D 83/06
(52) U.S. Cl. .................. 128/203.15; 128/203.12; 128/203.21; 128/203.23; 206/469
(58) Field of Search .................. 128/203.15, 203.12, 128/203.21, 203.23; 206/469

(56) References Cited

U.S. PATENT DOCUMENTS

| | | | |
|---|---|---|---|
| 5,669,973 A | 9/1997 | Pletcher | |
| 5,699,649 A | 12/1997 | Abvour et al. | |
| 5,714,007 A | 2/1998 | Pletcher | |
| 5,875,776 A | 3/1999 | Vaghefi | |
| 6,279,736 B1 * | 8/2001 | Hekal | 206/204 |

* cited by examiner

Primary Examiner—John G. Weiss
Assistant Examiner—Derwin P. Erezo

(57) ABSTRACT

A process for producing uniform small doses of finely divided substances that consists of forming a well mixed dispersion of a finely divided substance in a liquefied gas and then metering precise quantities of the mixture onto the surface of a containment vessel. A major application involves the packaging of fine pharmaceutical powders into small unit doses for inhalation therapy. Liquid nitrogen is the preferred liquefied gas. A liquefied noble gas may be employed as a dispersing medium for sensitive or highly reactive substances. Powder particle size reduction may be carried out in the liquid nitrogen medium with little or no damage to sensitive pharmacological materials. The atmosphere of the seated containment vessel is easily pressurized with nitrogen. The containment vessel may be seated prior to the total evaporation of the liquefied gas dispersing medium. The containment vessel is thus pressurized to relatively high pressures to facilitate the subsequent aerosolization of the pharmaceutical in an inhaler during inhalation therapy.

15 Claims, 1 Drawing Sheet

METHOD FOR PRODUCING UNIFORM SMALL DOSES OF FINELY DIVIDED SUBSTANCES

Figure 1:
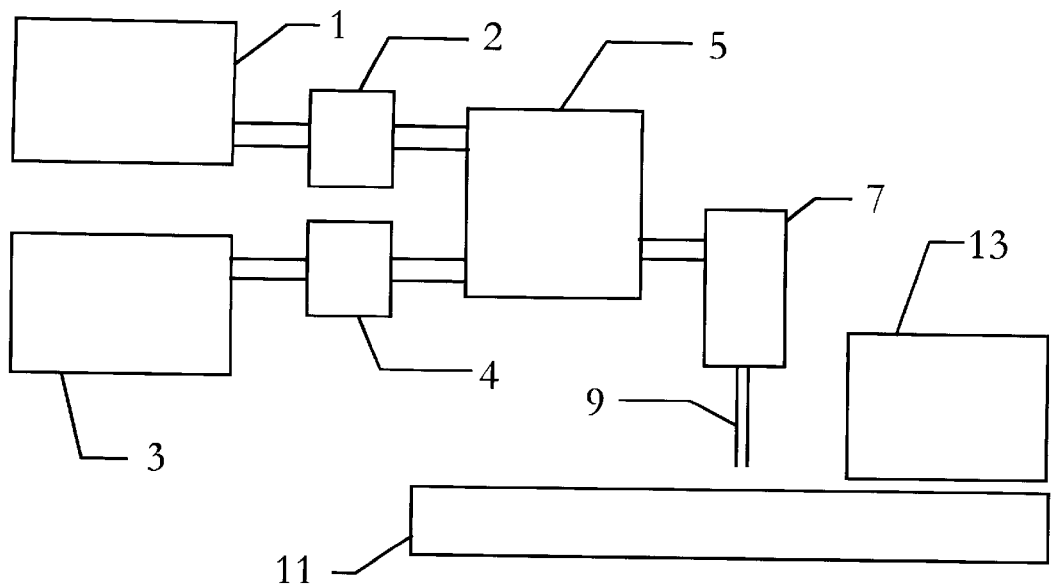
Figure 2:
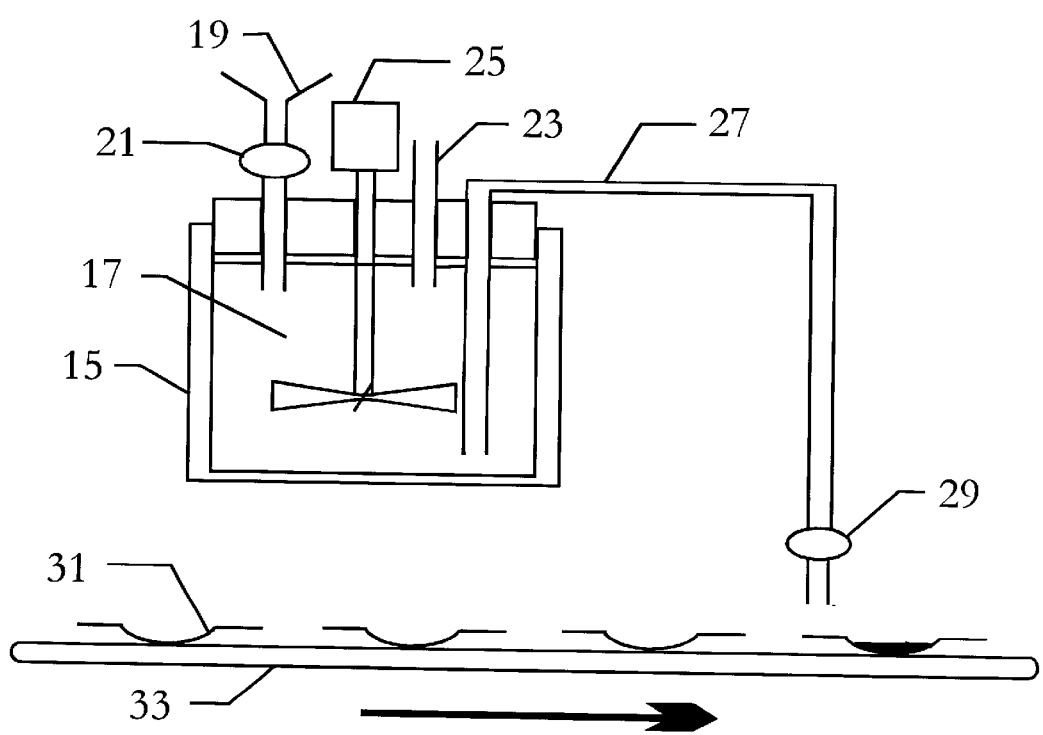

This application claims benefit of Provisional No. 60/106,338 filed Oct. 3, 1998.

This invention provides a method for producing uniform small doses of finely divided substances and more particularly, the invention relates to a technique employing liquid nitrogen as a dispersing medium for the purpose of packaging fine pharmaceutical powders.

BACKGROUND OF THE INVENTION

The therapy of lung disease often relies on inhaled medications. Bronchodilators have are widely employed in the treatment of asthma. Inhaled aerosolized antiviral agents are employed in the treatment of infectious diseases. Although most inhaled medications are given for their local effect, there is much recent interest in aerosol delivery of medications for systemic absorption. Inhaled drugs, in the form of very small dry powder particles, may be rapidly and directly absorbed into the blood stream. Thus, for example, proteins and peptides may be self-administered rather than administered by injection.

The list of drugs currently under investigation for inhalation delivery is quite extensive. Aerosolized insulin for diabetes is anticipated to become a major application of inhalation therapy.

Most large organic molecules, including proteins and peptides, are denatured by stomach acid when ingested. Absorption in the peripheral parts of the respiratory system overcomes this problem. Thus, the physician has means to provide the patient with a technique whereby the patient may self-administer large molecule medicaments without injection. The value of inhalation therapy in administering insulin, for example, is obvious.

Prior to the development of dry powder inhalers, most inhalation therapies employed pressurized chlorofluorocarbon propellants to disperse drugs. Environmental concern relating to CFC destruction of the earth's ozone layer has reduced the utility of this approach.

Dry powder inhalers for pulmonary drug delivery require dose levels that range from 25 micrograms to over 1,000 micrograms. Powder particle mean diameters of between 0.5 and 5.0 microns are required to provide effective deposition within the lung since larger particles tend to deposit in upper airways without any useful absorption to the circulatory system.

It is difficult to provide metered doses within the required tolerances at the 25 to 250 microgram levels. High-speed weighing systems are generally limited to dose sizes of about 5,0000 micrograms or greater and thus require the active pharmaceutical be diluted with an excipient, such as lactose powder, in order to increase the total measured mass. This dilution approach is subject to limitations in mixing uniformity and the aspiration of extraneous matter by the patient.

Another approach for low dose packaging involves dispersing the active powder in a medium that is in a liquid state at room temperature. The packaging substrate is then filled or coated and the liquid evaporated leaving the powder residue on the surface of the substrate. This approach has limitations in view of potential chemical reactions between the pharmaceutical medicament and the dispersing solvent. Government agency approvals are often required for the use of this process because of these potential interaction problems.

Yet another approach for low dose packaging involves the electrostatic precipitation of aerosolized medicament onto the surface of the medicament package. Abrams et al, U.S. Pat. No. 5,699,649, describe a system employing an endless belt which is charged, developed with an aerosolized powder, and the powder image then transferred to the package. The direct electrostatic precipitation of aerosolized powder is disclosed in Pletcher, U.S. Pat. No. 5,669,973. An improvement in this electrostatic precipitation apparatus is described by Pletcher et al, U.S. Pat. No. 5,714,007. These electrostatic deposition techniques require complex control equipment to accurately meter the required dosage into each package. The rate of powder deposition is also limited due to particle transit time effects and limitations in the mass density of the aerosol. Difficulties in re-aerosolizing the particles in the user's inhaler, because of the large electrostatic forces on the charged particles, may also be significant.

Many problems relate to the delivery of dry powder pharmaceuticals to the patient. Several devices rely on inhalation by the patient to provide the power to aerosolize the powder. Young patients, older patients, or patients with asthma often do not have the capacity to strongly inhale. Other inhalers rely on pressurized gas to disperse or aerosolize a powder. Vaghefi, U. S. Pat. No. 5,875,776, employs a gas cylinder to supply the energy required to rupture a sealed dosing cartridge. He also describes an alternate approach employing spring-loaded plungers to penetrate the airtight cover of dosing cartridges.

The present invention provides a cost-effective method for repeatedly filling unit dose packages with accurate masses of fine powder medicament. In addition, the invention provides a simple direct method for packaging fine powders under high pressures of nitrogen gas for subsequent rapid re-aerosolization in inhalers thus eliminating the requirement for an external aerosolizing power source.

SUMMARY OF THE INVENTION

The invention provides a process that uniformly mixes a pre-weighed amount of finely divided substance with a known volume or known weight of liquid nitrogen. A uniform dispersion of the powder in the liquid nitrogen medium is obtained after mixing. Small volumetric measures of liquid may then be drawn from the liquid reservoir and deposited onto the surface of a solid substrate. The liquefied nitrogen evaporates to form nitrogen gas leaving a low mass per unit area of finely divided substance on the surface of the substrate. The substrate may be slit, die-cut or otherwise formed into individual packages for use in dry powder inhalers. Alternately, metered liquid dispersions may be deposited into individual capsules, blister packs, or other forms of packaging pre-forms.

Metering and controlling the filling volume may be carried out using any of a number of well known high-speed filling line systems.

The advantages of employing liquid nitrogen in this application include:
1. Liquid nitrogen is chemically inert both because of its chemical makeup and extremely low temperature.
2. Liquid nitrogen is very low in cost; high volume prices are about twenty cents per pound.
3. Liquid nitrogen has a low viscosity, which is of value in processing and mixing.
4. Liquid nitrogen has a very low dielectric constant, which is useful in stabilizing dispersions.

5. The extremely low temperature of liquid nitrogen allows powders to be comminuted without fear of generating high temperatures, which might change the properties of the active ingredient.
6. At room temperature, liquid nitrogen rapidly evaporates.
7. The nitrogen gas realized from the evaporation of the liquid phase may be employed as an inert package atmosphere in the final product.
8. Because of the inert nature of the liquid, the active pharmaceutical may be stored for long periods of time prior to packaging.
9. Technologies for liquid nitrogen shipping, handling, storing, and carrying out processing operations, such as cryogenic grinding, are well developed.
10. A unit dose package may be sealed while still retaining a small amount of liquid nitrogen. As the package is warmed, the liquid nitrogen evaporates to pressurize the sealed package with an inert gas. The high pressure is valuable for re-aerosolizing the powder in the package when used in an appropriate inhaler.

In one embodiment of the invention, a known small mass of fine powder medicament is introduced into a known mass of liquid nitrogen that is contained in a Dewar cryostat. The mixture is stirred until the medicament powder is well dispersed. A small metered quantity of the dispersion is then introduced into a packaging blister. This operation is repeated to sequentially fill an assembly of blister packs. The liquid nitrogen is allowed to gradually evaporate and the blisters sealed, just as the last of the nitrogen liquid is vaporized, in order to maintain the sealed powder in a nitrogen atmosphere. The unit dose blisters are the labeled, bulk packaged and shipped to be utilized in unit dose respiratory inhalers.

In a further embodiment of the invention, the blister is sealed prior to the complete vaporization of the liquid nitrogen. A high pressure then develops in the package as the liquid nitrogen remaining in the package vaporizes. The user would insert the pressurized pack into his inhaler. During inhalation, the user would actuate a mechanism that ruptures the pack thus ejecting the powder, now completely aerosolized, into the air stream being inhaled.

BRIEF DISCRIPTION OF THE DRAWINGS

FIG. 1 shows a flow diagram illustrating material flow.

FIG. 2 depicts a typical liquefied gas fill line.

DETAILED DESCRIPTION

The general concept of the finely divided substance packaging process according to the present invention is schematically diagramed in FIG. 1. The finely divided substance filling system consists of a storage cryostat 5 in which the finely divided substance is mixed with a liquefied gas, typically liquid nitrogen, to form a uniform dispersion and stored pending the package fill operation. The liquefied gas is supplied through metering valve 2 from reservoir 1. A finely divided substance source 3 is employed as a reservoir of the finely divided substance that measured out employing metering device 4 for delivery to mixing cryostat 5. Filling line 11 sequentially transports substrates that are to receive a metered dose of dispersed powder under fin nozzle 9. Each metered dose is dispensed under control of metering valve 7. Post filling operations such as liquid medium evaporation, sealing, labeling, etc are carried out at filling line station 13

This fill system may operate in a batch mode. In this case, a measured quantity of liquefied gas together with a measured quantity of finely divided substance are periodically introduced into cryostat 5. Alternately, continuous feeds may be employed such that a constant volume of the figure mixture is maintained in cryostat 5.

The liquefied gas reservoir 1 is typically pressurized thus forcing the liquid through metering device 2. The handling and storage of liquefied gases as well as instrumentation for monitoring and controlling flow, temperature, liquid level, etc are well known. The Handbook of Cryogenic Engineering, edited by J. G. Weisend II, published by Taylor & Francis, 1998 describes many of these techniques in detail.

Finely divided substance stored in reservoir 3 may be fed using a metering device 4 in the form of a screw feeder either in a controlled continuous delivery or in an intermittent fashion. Alternately, metered feed device 4 may consist of a platform weighing mechanism that is loaded with a predetermined mass of powder and then fed, using vibration of the weighing platform to feed a measured mass of powder into a screw feeder that communicates with cryostat 5. More than one finely divided substance may be introduced into cryostat 5 when desired. Two or more materials may be premixed and added to reservoir 3 or, alternately, several reservoirs and metering devices may be employed in parallel to feed powders. In this case, it is very simple to modify the amounts of each added powder on a batch by batch basis.

Size reduction of the dispersed powder may be carried out without thermal damage to the powder in view of the low process temperature provided by employing a liquefied gas as the dispersing medium. This size reduction may be carried out in cryostat 5. The high pressure generated by evaporating cryogenic fluid may be employed to force the dispersion through a high-pressure valve homogenizer. Individual biological cells may be ruptured in this manner thus releasing proteins and enzymes from such cells. Alternately, size reduction may be carried out by employing a cryostat in the form of a stirred bead or a ball mill. Vibratory bead or ball mills may also be employed in this regard. These size reduction equipments are described in Perry's Chemical Engineers' Handbook, Seventh Edition, McGraw-Hill, Ch. 20 (1997). In addition to size reduction, the cryostat may also include filtering apparatus so that only selected particle size materials are introduced into metering valve 7.

Transport 11 operates intermittently to sequentially position receptor substrates 31 under fill nozzle 9. The unit dose receptor substrates may be in the form of an unsealed capsule, blister pack, film or foil, tube, or vial. Receptor substrates 31 are cooled prior to the filling operation in order to eliminate spattering of the filling mixture due to rapid evaporation of the liquefied medium. After filing, the filled receptor moves to sealing station 13 where the filled package is sealed. The sealing process depends upon the package configuration and material of construction.

A sufficient time interval is provided between time of filling and time of sealing to evaporate all or most of the liquefied gas. In most cases, it is preferable to maintain a slight positive pressure of a relatively inert gas such as nitrogen in the package. In some instances, it may be necessary to employ a noble gas such as argon or krypton as the packaging gas in order to prevent the degradation of extremely unstable substances.

The packaging method of the present invention may be employed with a variety of pharmaceuticals. Some contemplated examples illustrating the application range include the following: analgesics, sedatives, antianginal agents, anti-anxiety agents, antipsychotic agents, antiarrhythmics, antiarthritic agents, anticoagulants, anticarcinogens, thrombolytic agents antifibrinolytic agents, anticonvulsants, antiparkinson agents, antideprssants, antihistamines, antihypertensive agents, antibacterial agents, antifungal agents, antiviral agents, diabetes treatment agents, cancer chemotherapy agents, antimicrobials, anti-infectives, bronchodialators, hormones, hypoglycemic agents hypolipidemic agents, proteins, peptides, nucleic acids, specialized cells, antiulcer agents, antireflux agents, antinauseants, and the like. While the major application area involves pharmaceuticals, other potential applications of the present invention include packaging of specialty chemicals. Semiconductor doping agents, for example, may be packaged in precise small quantities. Powerful and expensive chemicals such as root growth hormone, chemical catalysts, and the like may be packaged using the method of the present invention.

Liquids and active substances dissolved or dispersed in a liquid may also be packaged or dispensed employing the method of the present invention. In this case, fill nozzle 9 is terminated with a spray nozzle. The substance to be packaged or dispensed is now sprayed directly into the liquefied dispersing medium. The liquid phase of the substance to be packaged is instantly frozen and now behaves as a solid that may be manipulated, including arty particle size reduction operation, the same as any solid fine powder.

One embodiment of the present invention provides for packaging the medicament under a relatively high pressure of the packaging gas. Upon rupture in an appropriate inhaler, the powder material is aerosolized thus providing the fine distribution of powder required of inhalation therapy. Methods of sealing under pressure are well known to those skilled in the packaging of pharmaceuticals and foods.

FIG. 2 is a schematic illustration of a liquefied gas packaging station. Cryostat 15 is filled with liquefied gas; 17, typically liquid nitrogen, from fill tube 23. A metered quantity of powdered medicament is introduced at powder loading port 19 and metered by metering valve or screw 21. The dispersion is well mixed using mixer 25, shown here as a motor driving an impeller blade. Evaporating nitrogen creates a positive pressure in the cryostat to drive the mixture through fill tube 27 to fill valve 29. As packaging blisters 31 are carried through the fill station by package transport 33, they are filled with a predetermined volume of liquid using metering valve 29. After filling, the liquid gas is allowed to evaporate and the blister sealed using thermocompression bonding or an adhesive.

Although blisters ire shown in FIG. 2, capsules, thin plastic films, preformed pellets, linear and circular arrays of blister packs, semiconductor chips, etc. may also be filled or coated using the method of this invention.

If the package is sealed prior to the complete evaporation of liquid nitrogen, the gas pressure will build up in the sealed vessel. Since the density of gaseous nitrogen is less than $1/1,000$ that of liquid nitrogen, most of the liquid nitrogen must be vaporized prior to sealing. Control of the package pressure may be carried out by using a closure lid that is held in place with a controlled pressure and when the internal package pressure becomes equal to the applied pressure, the closure lid may be thermocompression bonded or crimped to form the package seal.

The cost effectiveness of this filling process may be noted by considering the following example.

A 200-liter Dewar flask is filled with 200 liters of liquid nitrogen to which is added 5 grams of pharmaceutical powder to be ultimately employed in a dry powder inhaler. The mixture is thoroughly stirred to fully disperse the powder. A continuous line of blister packs is passed under a metering device that precisely transfers one milliliter of fluid into each pack. Each dose then contains $5/200,000$ of a gram or 25 micrograms. The blister packs are filled in a moving line containing ten blister packs across the line width. Ten metering fill units are spaced across this line so that ten packs are filled simultaneously; each filled with a powder dry weight of 25 micrograms. Each fill unit is capable of filling 5 packs per second so that a total of 50 packs are filled each second or 180,000 packs are filled each hour. The packs may be sealed just as the last liquid nitrogen is vaporized so that the packs are then sealed in an inert nitrogen atmosphere under a slight positive pressure. This is a batch process and thus two complete fill systems must be employed to continuously operate a fill line. The cost of liquid nitrogen used in each unit dose preparation is about $4/100$ of a cent.

While the invention has been described with reference to the structures disclosed herein, it is not confined i:o the details set forth and this application is intended to cover such modifications or changes as may come within the purposes of the improvements or the scope of the following claims.

What is claimed is:

1. A method for packaging uniform small measures of a finely divided substance that comprises the steps of:

providing a packaging receptor substrate, forming a mixture of said finely divided substance with a liquefied gas, agitating said mixture to form a uniform dispersion, dispensing a metered quantity of said uniform dispersion onto a surface of said receptor substrate, allowing a substantial portion of said liquefied gas to evaporate from said dispensed metered quantity; and sealing said receptor substrate to form an airtight chamber.

2. The method of claim 1 where said liquefied gas is liquid nitrogen.

3. The method of claim 1 where said liquefied gas is selected from the group of liquefied noble gases.

4. The method of claim 1 where said finely divided substance is selected from the group of pharmaceutical powders employed in inhalation therapy.

5. The method of claim 1 where said finely divided substance has a mean particle diameter between about 0.5 micrometers and about 5 micrometers.

6. The method of claim 1 where said receptor surface comprises a blister pack.

7. The method of claim 1 where said receptor surface comprises at least one internal surface of a capsule.

8. The method of claim 1 where said receptor surface comprises at least one internal surface of a vial.

9. The method of claim 1 where said finely divided substance is formed by comminuting said finely divided substance in the presence of said liquefied gas.

10. A method for packaging uniform small measures of a finely divided substance that comprises the steps of:

providing a packaging receptor substrate, forming a mixture of said finely divided substance with a liquefied gas, agitating said mixture to form a uniform dispersion, dispensing a metered quantity of said uniform dispersion onto a surface of said receptor substrate, allowing a portion of said liquefied gas to evaporate from said dispensed uniform dispersion, and sealing said substrate to form an airtight seal prior to complete evaporation of said liquefied gas, whereby said sealed substrate is maintained under high pressure.

11. The method of claim 10 where said high pressure is between about 20 pounds per square inch and about 300 pounds per square inch.

12. The method of claim 10 here said liquefied gas is liquid nitrogen.

13. The method of claim 10 where said liquefied gas is selected from the group of liquefied noble gases.

14. The method of claim 10 where said finely divided substance is selected from the group of pharmaceutical powders employed in inhalation therapy.

15. The method of claim 10 where said finely divided substance has a mean particle diameter between about 0.5 micrometers and about 5 micrometers.

* * * * *